United States Patent [19]

Taniguchi et al.

[11] Patent Number: 4,800,155

[45] Date of Patent: Jan. 24, 1989

[54] HUMAN MONOCLONAL ANTIBODY TO LUNG CARCINOMA AND HYBRIDOMA PRODUCING THE SAME

[75] Inventors: Masaru Taniguchi, 17-12, Konakadai 3-chome, Chiba-shi, Chiba; Hiroaki Saito, Chiba; Yutaka Yamaguchi, Chiba; Fumio Hiraoka, Chiba; Ikuro Nakamura, Tokyo, all of Japan

[73] Assignees: Yoshitomi Pharmaceutical Industries, Ltd., Osaka; Masaru Taniguchi, Chiba, both of Japan

[21] Appl. No.: 12,459

[22] Filed: Feb. 9, 1987

[30] Foreign Application Priority Data

Feb. 7, 1986 [JP] Japan .................................. 61-26544
Mar. 10, 1986 [JP] Japan .................................. 61-52264

[51] Int. Cl.⁴ .................. G01N 33/53; G01N 33/577; C12N 5/00; C07K 15/14
[52] U.S. Cl. .......................................... 435/7; 435/68; 435/172.2; 435/240.27; 436/503; 436/518; 436/548; 436/813; 530/387
[58] Field of Search ............... 436/548, 811, 813, 513, 436/800, 804, 518, 503; 435/7, 68, 172.2, 240.27; 935/95; 530/387; 424/85

[56] References Cited

U.S. PATENT DOCUMENTS

| | | | |
|---|---|---|---|
| 4,661,586 | 4/1987 | Levy et al. | 435/172.2 |
| 4,677,070 | 6/1987 | Larrick et al. | 435/70 |
| 4,678,747 | 7/1987 | Lloyd et al. | 435/68 |
| 4,683,200 | 7/1987 | Hirohashi et al. | 435/68 |
| 4,708,930 | 11/1987 | Kortright et al. | 435/95 |

FOREIGN PATENT DOCUMENTS 0124717 of 1984 United Kingdom ................ 436/548

OTHER PUBLICATIONS

Murakami et al, In Vitro Cellular & Developmental Biology, vol. 21, No. 10, 1985, pp. 593–596.

*Primary Examiner*—Robert J. Warden
*Assistant Examiner*—Florina B. Hoffer
*Attorney, Agent, or Firm*—Sughrue, Mion, Zinn, Macpeak & Seas

[57] ABSTRACT

A human-mouse hybridoma producing a human monoclonal antibody specific for human lung squamous and adenocarcinomas. The human monoclonal antibody can be utilized as a diagnostic agent in serological diagnosis, in the radioimmaging of lung tumors or as a therapeutic agent.

5 Claims, 5 Drawing Sheets

HUMAN MONOCLONAL ANTIBODY TO LUNG CARCINOMA AND HYBRIDOMA PRODUCING THE SAME

BACKGROUND OF THE INVENTION

By establishment of the hybridoma method by Köhler and Milstein (1975), it has been made possible to fuse antibody-producing B cells incapable of conducting persistent culture with myeloma cells capable of conducting persistent culture thereby to produce continuously growing B cell hybridoma while producing antibody (Köhler et al., Nature, 256, 495, 1975). Using this method, many monoclonal antibodies which react with desired antigens have been produced. Further human monoclonal antibodies have also been produced by transformation of lymphocytes using EBV (Epstein-Barr virus), etc., in addition to cell fusion between human lymphocytes and mouse myeloma cells or human myeloma cells.

Monoclonal antibodies to malignant tumor cells are utilized for basic investigations such as analysis of tumor antigens, etc. In addition, clinical applications including serological diagnosis, radioimaging of tumor using labeled antibodies, administration of antibodies having anti-tumor effect in vivo, etc. have also been attempted gradually.

At present, cancer therapy has been made synthetically by combining surgical therapy, chemotherapy, radiotherapy, immunotherapy, etc. These therapies are also freely applied to lung cancer but relapse due to local and remote metastasis is not unusual so that lung cancer is unfavorably prognostic among cancers. Under such circumstances, it is indispensable to produce monoclonal antibody to lung cancer, from an aspect of new specific immunotherapy adds to the treatments of lung cancer. Mention may be made of monoclonal antibodies capable of reacting with human lung cancer in, for example, Published Unexamined Japanese Patent Application Nos. 60-58926 and 60-199830, EP-156578-A, EP-155172-A.

However, anti-lung cancer monoclonal antibodies currently produced as above are mouse monoclonal antibodies which are produced by hydriboma obtained by cell fusion of antibody-producing cell of a mouse immunized by human lung cancer cell lines and mouse myeloma. These mouse monoclonal antibodies are foreign matters to human so that they are unsuited for direct administration in the living body and it has been desired to produce human monoclonal antibody having high reactivity.

Among methods for producing human monoclonal antibodies currently attempted, the human-human hybridoma method involves disadvantages that human myeloma cells having a good fusion efficiency comparable to mouse myeloma cells have not been established yet, stable antibody-producing clones are obtained only with difficulty even by the EBV method, handling and separation of virus are difficult, etc. Further the production of monoclonal antibody to human lung cancer cells by the human-mouse heterohybridoma method has not been succeeded on a full scale.

SUMMARY OF THE INVENTION

As a result of extensive investigations, the present inventors have produced human monoclonal antibody capable of highly reacting with human lung squamous and adenocarcinomas and human-mouse hybridoma which grows while stable producing the antibody.

Namely, the present invention relates to human-mouse hybridoma which is obtained by cell fusion of antibody-producing human lymphocytes of lung cancer patient and mouse myeloma cells and human monoclonal antibody produced by the human-mouse hybridoma.

DISCLOSURE OF THE INVENTION

The human monoclonal antibody of the present invention has the following properties:

(i) It is reactive over a wide range, e.g., with human lung cancer cell lines and excized human lung cancer tissues of various histological types including 100% (29/29) squamous lung cancer, 70% (14/20) adeno lung cancer and 37.5% ($\frac{3}{8}$) large cell lung carcinoma (excluding lung small cell carcinoma), but scarecely reacts with normal human fibroblast and normal tissue.

(ii) It reacts with various other malignant (e.g. thyroid cancer, breast cancer, esophagus cancer, stomach cancer and extra hepatic bile duct cancer etc.) but not benign tumor tissues to some extent.

(iii) The antibody class is IgM class and light chain type is λ; it has a complement binding ability and complement-dependent cytotoxicity.

(iv) It recognizes antigen molecule having a molecular weight of about 200Kd according to the SDS-PAGE method on the surface of PC10 (a human lung squamous cell line) cell membrane which is divided into components having molecular weights of about 65Kd according to the SDS-PAGE method in a reducing condition; etc. and is an antibody having high reactivity to lung cancer tissue. Further the human-mouse hybridoma producing the same is stable over long periods of time because the hybridoma produces λ-light chain antibody.

According to the present invention, the hybridoma producing the human monoclonal antibody was established by cell fusion of lymph node cells from patient with human lung squamous cancer and mouse myelona cells in the presence of a cell fusion agent, culturing in a selection medium and cloning hybridoma producing the desired antibody in the obtained fused cells. The stable hybridoma over long periods of time which produces an antibody capable of widely reacting with human lung cancers can be obtained by using lung cancer cell line especially having different tissue type as a target cell or additional operation for selecting λ-light chain, upon cloning. By further culturing this hybridoma, the human monoclonal antibody of the present invention can be produced.

Hereafter these steps will be described in more detail.

(I) Production of Hybridoma (a) Antibody-producing cell

The antibody-producing cells which are used for cell fusion according to the present invention are human lymphocytes from lung squamous cancer patient. Human lymphocyte populations of lung cancer patient are expected to contain any of cells that can produce antibodies capable of reacting with human lung cancer cells. Therefore, lymphocytes from lymph nodes belonging to the removed portion upon operation of the patient with lung cancer, etc. can be used.

The antibody-producing cells that can be used in the present invention are lymphocytes of lymph nodes belonging to the removed portion upon operation of the squamous cell carcinoma patient. When lymph nodes belonging to the removed portion are too close to tumor, immune tolerance occurs to the tumor; conversely when too remote, problems arise that a sensitized state of lymphocytes is inappropriate, etc. Therefore, it is appropriate that mediastinal lymph nodes which are most suitably sensitized be selected for the fusion to establish anti-lung cancer antibody producing hybridomas.

(b) Myeloma cell

As the myeloma cells, conventional mouse-derived established cell lines are used. Examples include P3-X63-Ag8-U1 (P3US), SP2/0-Ag14 (SP-2), P3-X63-Ag8-6.5.3 (X63.6.5.3), P3-X63-Ag8 (X63), P3-NS-1-1-Ag4-1 (NS-1), MPC11-45.6.TGI.7 (MPC-11), S194/5XX0.BU.1 (S194), etc. These cell lines are resistance to 8-azaguanine (AZG) or 6-thioguanine and can be selected in hypoxanthine-aminoputerine-thymidine (HAT) medium; among them, particularly preferred myeloma cell lines are non-immunoglobulin-secreting myeloma cells. These myeloma cells are subcultured in normal media from which 8-azaguanine or 6-thioguanine removed, about 2 weeks before the fusion and, on a day of the fusion, cells in the exponential growth phase are used. The normal media can be used any of media in which animal culture cells can grow, for example, RPMI 1640 containing 10% fetal calf serum (FCS), Dulbecco's modified medium (DMEM), etc. are used.

(c) Method of Cell Fusion

The cell fusion is carried out by mixing the aforementioned human lymph node cells and mouse myeloma cells in a cell number ratio of 2.5 to 5:1 and treating the mixture in the presence of a fusion agent. As the fusion agent, there can be used polyethylene glycol (PEG, molecular weight of 1000 to 6000), polyvinyl alcohol, Sendai virus (HVJ) and its inactivated products, etc. Further, electric fusion can also be used. However, it is appropriate to use PEG having a molecular weight of 1500. The fusion is carried out as follows: both cells are once brought into close contact by centrifugation. Then, the cells are mixed to fuse membranes over several minutes, while gently adding the fusion agent thereto. Thereafter, the fusion mixture is gradually diluted in a serum-free medium and the supernatant is removed by centrifugation. After the cells are suspended in 10% FCS-containing RMPI 1640 medium, the suspension is separately inoculated in a 96-well flat bottom plate in 2.5 to $5 \times 10^5$ cells/well followed by incubation.

(d) Selection of Fused Cell

From next day after the incubation, a half amount of the medium in the well is replaced with HAT medium supplemented with hypoxanthine, aminoputerine and thymidine or its modified medium to stepwise increase the aminoputerine concentration in the medium. In this selection medium, the myeloma cells and human lymphocytes that failed to fuse are killed but fused cells alone grow in the medium. When extremely small number of cells are seeded in the wells, feeder cells may be used to assist growth of the desired cells. As the feeder cells, thymocytes, peritoneal exudate cells, or spleen cells of intact animals, etc. can be used. The fused cells selected in HAT medium are stepwise transferred to ordinary media, considering the possibility that aminoputerine would remain in the medium.

(e) Detection of the desired antibody-producing hybridoma

From the fused cells obtained as described above, the desired antibody-producing hydridomas are detected. For the detection, enzymeimmunoassay (EIA) method, radioimmunoassay (RIA) method or fluorescence-activated cell sorter (FACS), etc. can be utilized. In the present invention, in order to accurately detect the desired antibody-producing hybridomas, ELISA method using cells as target is used. According to this method, established human lung cancer cell lines are previously cultured and the cell suspension is separately dispenses in a 96-well microplate at a concentration of, e.g., $1 \times 10^5$ cells/well upon assay, without immobilization with glutaraldehyde. After centrifugation, the supernatant is flicked out from the plate and about 20 $\mu$l of the culture supernatant of hybridoma is added thereto. After reacting at room temperature for an hour, washing and centrifugation are repeated and followed by reacting with alkali phosphatase conjugated anti-human antibody. After washing and centrifugation, a enzyme substrate (for example, disodium p-nitrophenylphosphate) is used to develop a color, whereby its absorbance is measured with microplate photometer.

In this case, by using lung cancer cell line derived from the same tissue type (squamous cell carcinoma in the present invention) as that of lung cancer of the patient from which lymphocytes used for the cell fusion have been removed and at the same time, lung cancer cell line derived from a different tissue type as a target, the antibodies capable of widely reacting with human lung cancer can be detected.

(f) Identification of class and subclass of immunoglobulin

Class and subclass of immunoglobuline is determined by ELISA method or Ouchterlony's method (Menekigaku Jikken Nyumon (Guide to Immunological Experiment), Seibutsugaku Jikkenho (Method for Biological Experiment), 15, 75, 1982), etc.

(g) Establishment of stable hybridoma having a high antibody productivity

The thus obtained hybridoma should be cloned as early as possible. For the method of cloning, the limiting dilution method and the soft agar method are ordinarily used. The limiting dilution is preferably used and in this case, SD rat thymocytes, etc. can be added as feeder cells, if necessary, for purposes of assisting proliferation of the hybridoma. Further, in this case, clones which continue to produce monoclonal antibodies stably over long periods of time also be selected based on the light-chain class determined by the method of (f) described above. Namely, in the human-mouse hybridoma, the second chromosome of human in which a gene of $\kappa$-light chain is present is easily deleted so that antibody production is unstable but it is difficult to expect stable cell line over long periods of time. It is preferred that after $\lambda$-light chain antibody-producing cell line is selected as described above, ELISA method is again conducted using lung cancer cell line as a target to select clones producing antibodues capable of specifically reacting with human lung cancer in large quantities.

(h) Storage of hybridoma

The thus produced hybridoma and clone (subline) are suspended in freezing medium (FCS containing 5 to 10% dimethylsulfoxide (DMSO) or glycerol) at concentrations of $10^6$ to $10^7$ cells/ml, broken down to suitable amounts and freezed.

(II) Production of human monoclonal antibody

The hybridoma verified to secret the desired antibodies at the foregoing steps (a) through (g) can provide large quantities of antibodies by culture in vitro or in vivo. As the in vitro culture, spinner culture or static culture can be used and as the in vivo growth, there is used a method in which the hybridoma is transplanted to animal capable of transplanting tumor cells, e.g., nude mouse or nude rat, etc. and the antibodies are obtained from the ascites or blood.

Purification of the antibodies obtained from the culture solution, ascites, etc. can be performed in a conventional manner generally used for separation of protein, for example, salting out, centifugal separation, dialysis, various chromatographies, ultrafiltration and freeze drying, etc. in combination.

The antibodies of the prsent invention can be stored in various buffer solutions such as sodium chloride-containing phosphate buffer (PBS) and those further containing azides appropriately, etc., and utilized generally as the stable antibody solution.

(III) Reactivity with vital tissue

In order to examine the specificity of the produced monoclonal antibody in more detail, freshly frozen slices were prepared from a tumor specimen removed upon operation of the patient with lung cancer and normal tissue upon autopsy and immobilized for 30 minutes at −20° C. in an immobilizing solution of 90% ethanol, 5% acetic acid and 5% distilled water. The prepared monoclonal antibody and FITC (fluorescent isothiocyanate) or peroxidase conjugated anti-human antibody were used as a primary antibody and a secondary antibody, respectively and, tissue staining was performed using the indirect immunofluorescent or immunoperoxidase technique thereby to microscopically examine the staining. In the present invention, tumor tissue was determined depending upon the degree of staining as being positive when reacted, and negative when not reacted. Further, the normal tissue was determined by comparison with the positively reactive tumor tissue used as a control, as being weakly positive (±) when the reactivity was obviously weak, positive (+) when it was stained as almost the same as the tumor tissue and negative (−) when not reacted.

(IV) Utility of 4G12 monoclonal antibody

The antibody of the present invention can be labeled, e.g. with radioactive or fluorescent label, and used to identify lung cancer cells. Furthermore, the antibody can be used therapeutically to treat patients suffering from lung cancer; the antibody can be administered to the patient alone or can be administered coupled to a cytotoxic agent.

Namely, the antibody can be used to detect lung cancer cells, or the antigen of lung cancer in plasma and other body fluids, both in vivo and in vitro. For in vivo detection of lung cancer cells, the antibody can be radiolabeled by using conventional techniques and, in conjunction with conventional in vivo imaging techniques to detect labeled immune complexes. The labeled antibody can be administered to a patient and used to identify tumor sites in the patient. The antibody can also be used to measure the amount of the antigen of lung cancer in a clinical sample for early detection of disease or for monitoring tumor bulk.

Figure 1:
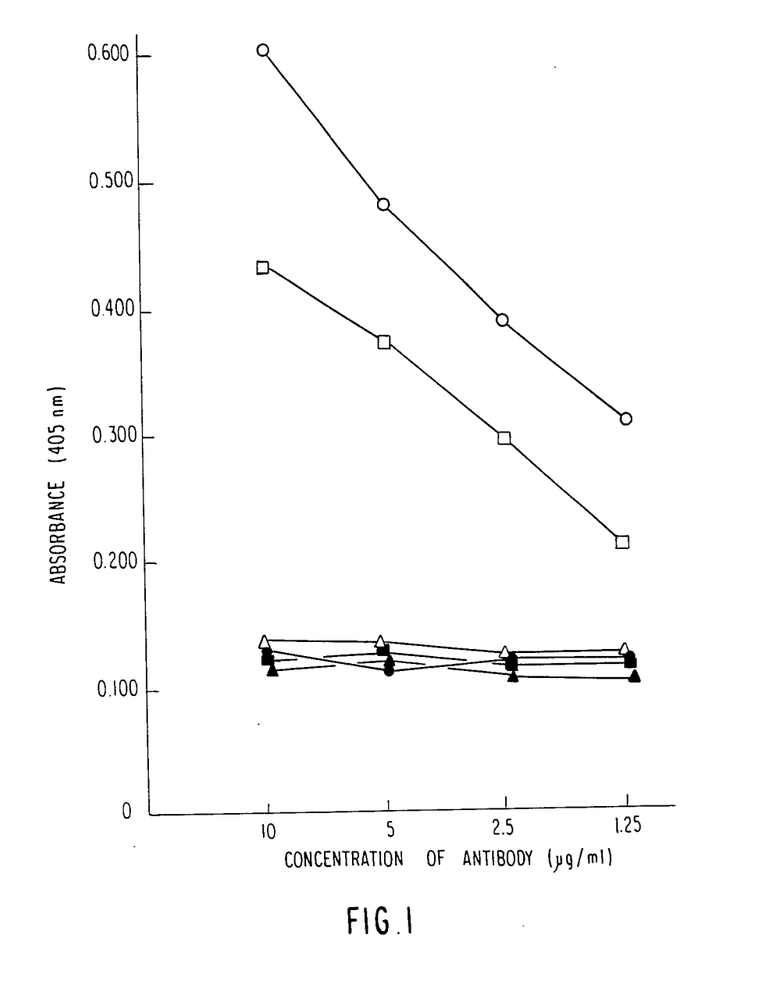

The monoclonal antibody produced according to the method of the present invention has the following properties:

(1) It reacts with human lung squamous cell carcinoma cell line (PC10) and human lung adenocarcinoma cell line (PC14) but does not react with human adult skin-derived fibroblast cells (FIG. 1).

(2) Among tumor slice specimens of tumor tissue removed upon operation of the lung cancer patient, it reacts with lung squamous cell carcinoma, lung adenocarcinoma and lung large cell carcinoma in rates of 29/29, 14/20 and ⅜ respectively but does not react with lung small cell cancer and other mediastinal tumors (Table 1).

(3) It never reacts with normal tissues except for trachea (gland cells), bronchi (grand cells) and kidney (renal tubular cells)(Table 2), and it dose not react with benign tumors (Table 4).

(4) It reacts with nonpulmonary tumor tissues such as thyroid cancer, breast cancer, esophagus cancer, stomach cancer and extra hepatic bile duct cancer in rates of 1/5, 2/5, 3/5, 2/5 and 1/5 respectively (Table 3).

Figure 2:
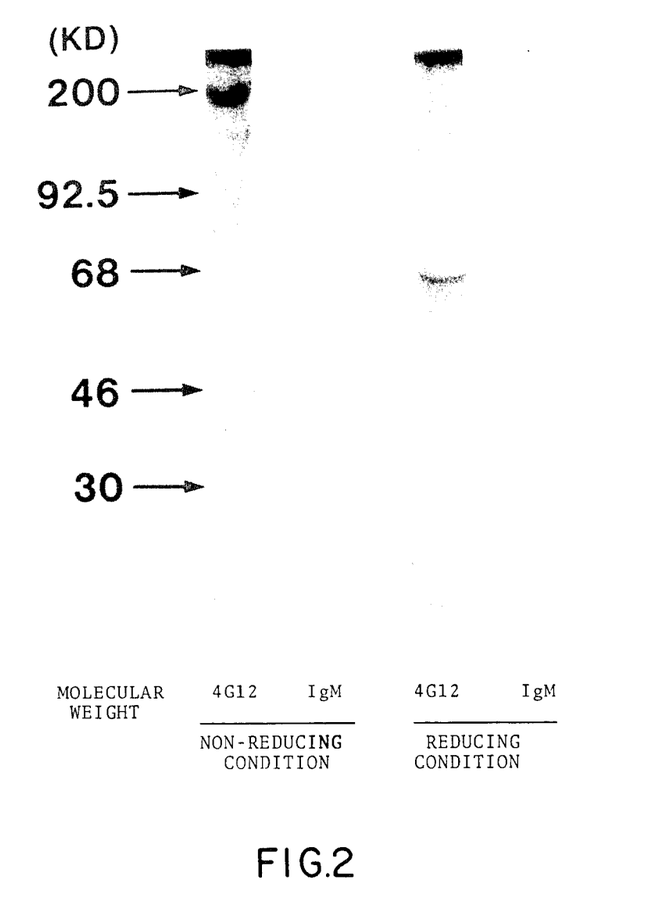
FIG. 2 shows SDS-polyacrylamide gel electrophoresis of an antigen on the PC 10 cell surface having a reactivity with 4G12 monoclonal antibody.

(5) It recognizes an antigen molecule having a molecular weight of about 200Kd according to the SDS-PAGE method in the soluble fraction on the surface of cellular membrane on PC10 cells which is divided into components having molecular weights of about 65Kd according to the SDS-PAGE method in a reducing condition (FIG. 2).

(6) The class of the antibody is IgM and light chain type is λ.

(7) It has a complement-binding ability and has complement-dependent cytotoxicity (FIG. 4), etc.; and it is noted that the monoclonal antibody is an antibody having high reaction to lung cancers and reacts with other cancers having a common antigen with human lung cancer but scarecely reacts with normal human tissues and benign tumors.

Further, the antibody of the present invention takes λ-light chain so that the human-mouse hybridoma produced thereby is stable over long periods of time.

The thus obtained monoclonal antibody which has a high reaction to lung cancer tissues can be widely utilized as an agent for investigations on lung cancers or as a diagnostic and therapeutic agent, such as serological diagnosis, radioimaging of tumor using labeled antibody, administration of the antibody having an antitumor effect, etc., in addition to basic investigations such as analysis of tumor antigen, etc.

BRIEF DESCRIPTION OF THE DRAWINGS

FIG. 1 shows the reactivity of 4G12 monoclonal antibody with cell line determined by the ELISA (Enzyme linked immunosorbent assay) method using cells as target. In the figure, the following symbols mean the reactivity in each combination of:

○—○ : PC10 cells and 4G12 monoclonal antibody

●—● : PC10 cells and the culture supernatant of P3U1 cells

□ □: PC14 cells and 4G12 monoclonal antibody

■—■: PC14 cells and the culture supernatant of P3U1 cells

△—△: fibroblast cells and 4G12 monoclonal antibody

▲—▲: fibroblast cells and the culture supernatant of P3U1 cells

FIG. 4 shows cytotoxicity of 4G12 monoclonal antibody. In the figure, the following symbols show the cytotoxicity in combination of:

● ●: PC10 cells, 4G12 monoclonal antibody and guinea pig complement
○ ○: PC10 cells, human IgM antibody and guinea pig complement
△ △: PC10 cells and 4G12 monoclonal antibody.

FIG. 5 shows stability of 4G12 monoclonal antibody-producing hybridoma. In the figure, symbol A shows 4G12 monoclonal antibody-producing cells screened after cell fusion, symbol B is cells after first cloning, symbol C is cells after second cloning and, symbols D through H show stability of the 4G12 monoclonal antibody-producing cells obtained in C with passage of day. Further, in the figure, marks ■ and □ show the reactivity of 4G12 monoclonal antibody with PC10 cells and the reactivity of the P3U1 cell culture supernatant and PC10 cells measured by absorbance (405 nm) by the ELISA method using cells at target and mark ▨ shows an antibody concentration produced in the culture supernatant in the hybridoma of the present invention.

Hereafter the present invention will be described concretely but is not deemed to be limited to these examples.

EXAMPLE 1

(1) Preparation of lymphocytes in lymph node belonging to the lung squamous cell carcinoma patient Lymph node belonging to lung squamous cell carcinoma patient was aspectically removed. After superfluous fat tissue was taken out in RPMI 1640 medium, the lymph node was passed through a steel mesh to separate into each lymphocyte. Washing and centrifugation were repeated in RPMI 1640 medium to remove carbon powder, etc. were contained in the lung cancer lymph node. Finally, a single cell suspension of RPMI 1640 medium was obtained.

(2) Cell fusion

A suspension of RPMI 1640 medium containing $4 \times 10^7$ mouse myelona cells P3U1 (Curr-Top. Microbiol. Immunol., 81, 1–7, 1978) and the suspension of RPMI 1640 medium containing $2 \times 10^8$ spleen cells prepared in (1) above were charged in a 50 ml tube followed by centrifugation at room temperature in $400 \times g$ for 5 minutes. The supernatant was completely removed and the tube was put in a incubator at 37° C. While gently stirring the cells with a tip of a pipette, 1 ml of warm 50% polyethylene glycol (PEG) solution was added over a minute. After stirring for further 1 minutes with the same pipette, 2 ml of RMPI 1640 medium warmed at 37° C. was added thereto over 2 minutes with gently stirring followed by centrifugation at room temperature in $400 \times g$ for 10 minutes. The supernatant was sucked. After 40 ml of RPMI 1640 medium containing 10% FCS was added and the mixture was gently stirred, this cell suspension was separately charged in a 96 well flat bottom microplate by 0.1 ml each followed by incubation at 37° C. in a humid 5% $CO_2$ atomosphere.

(3) Selection of fused cell

Next day after initiation of the incubation, 0.1 ml of HAT medium was added to each well of the 96 well flat bottom microplate. On Days 2, 3, 4, 6, 8 and 10, a half of the supernatant of each well was sucked and 0.1 ml of fresh HAT medium was supplemented to exchange the medium. Thereafter the medium exchange was performed with HT (hypoxantine-thymidine) medium every other day and fused cells were finally cultured in 10% FCS-containing RPMI 1640 medium.

(4) Detection of the desired antibody-producing hybridoma

The supernatant in the well in which colonies had been formed was measured using the ELISA method. Three kinds of PC10 (lung cancer cell line of human squamous cell carcinoma type), PC14 (human lung adeocarcinoma cell line) and normal human fibroblast cell line were used as target cells. Each target cell were dispensed in a 96 well microplate by $1 \times 10^5$ cells each and 20 μl of the culture supernatant of each colony was added thereto to react at room temperature for 60 minutes. After the cells were washed by centrifugation, 20 μl of alkali phosphatase conjugated rabbit anti-human antibody was added thereto to react them to room temperature. After the cells were washed again by centrifugation, a chromophoric substrate and a bufferee for color formation were added to the cells to form a color, thereby examining the reactivity with the target cell. The color forming degree was measured at absorbance of 405 nm with a microplate photometer. A well showing absorbance of more than twice that of the control (the culture supernatant of P3U1) was designated a positive well. Thus, hybridoma which reacted with the tumor cell lines PC10 and PC14 but did not react with normal human fibroblast cells was obtained.

(5) Reactivity with vital tissue

With respect to the hybridoma screened by the aforementioned ELISA method using cells as target, the reactivities with the tumor tissue removed from the lung cancer patient and normal tissue obtained upon autopsy were determined using the indirect fluorescent antibody technique. The activity was measured by the presence or absence of staining. Those that showed a high reactivity with the tumor tissue but did not react with the normal tissue were cloned by limiting dilution. In this case, the cell number of the hybridoma was adjusted to a concentration of 30 cells/20 ml using SD rat thymocytes were as feeder cells (feeder layer). The hybridoma was separately inoculated in a 96-well flat bottom microtiter plate by 0.2 ml each followed by incubation. When colonies grew to an appropriate size, their reactivities with the tumor tissue and the normal tissue were again determined by the indirect fluorescent antibody technique. Hybridoma 4G12 was obtained as a stable strain producing the antibody in large quantities.

(6) Purification of antibody

For purification, either the culture supernatant obtained by in vitro incubation of the hybridoma or ascites containing the antibody obtained by intraperitoneally administering 1 to $3 \times 10^7$ hybridomas to BALB/c nude mouse was purified. A 10-fold concentrate of 1300 ml of the culture supernatant with Aquaside (Kalbiochem) or about 10 ml of the ascites collected were centrifugated and each supernatants was charged in a dialysis tube followed by dialysis for 48 hours with 0.001M phosphate buffer (pH 6.0). By this procedure the desired monoclonal antibody could be precipitated. The precipitated monoclonal antibody can be handled as a soluble antibody by dissolving in a small amount of 3% sodium chloride aqueous solution and dialyzing the solution with 0.1M phosphate-sodium chloride buffer (pH 7.2).

(7) Identification of each class and subclass of immunoglobulin

Each class and subclass of immunoglobulin were identified by the ELISA method using specific antibody to each class and subclass of anti-human immunoglobulin and anti-light chain antibody. As a result, 4G12 monoclonal antibody was identified to the IgM. λ type.

(8) Property of 4G12 monoclonal antibody (i) Reactivity with established cell lines With respect to human lung squamous carcinoma cell line (PC10) and human lung adenocarcinoma cell line (PC14) as established cells and human adult skin-derived fibroblast cells as a normal cell, each reactivity was examined by the ELISA method. The results are shown in FIG. 1. It is evident that 4G12 monoclonal antibody shows a remarkable reactivity with human lung cancer cell lines (PC10 and 14).

(ii) Reactivity with tumor and normal tissues

The reactivity of 4G12 monoclonal antibody with each tissue was examined by the indirect immunofluorescent or immunoperoxidase technique. The results are shown in Table 1, 2, 3 and 4. It is evident that the human monoclonal antibody of the present invention highly reacts with human lung cancers and can be reative with nonpulmonary tumor tissues such as thyroid cancer, breast cancer, esophagus cancer, stomach cancer, extra hepatic bile duct cancer, etc. but scarecely reacts with normal human tissues and benign tumors.

(iii) Accumulation of 125I-labeled 4G12 monoclonal antibody in human lung cancer xenograft.

Accumulation of radiolabeled 4G12 monoclonal antibody was investigated by autoradiography. The technique of whole body autoradiography was used to study the accumulation of radioactive 4G12 monoclonal antibody in sections of the tumor-bearing nude mice. Seven days after the $^{125}$I-labeled antibody injection (50 μCi: specific activity is 1 μCi-μg), mice were sacrificed, freeze-dried and sliced 40 μm thick with an autocryotome. Sections were air-dried for 24–48 hours at 4° C. and then exposed to an X-ray film at room temperature for 2–4 days in light-tight boxes.

The radioactivity was specifically accumulated in the tumor region. The radioactivity of 4G12 monoclonal antibody when expressed as a persent dose/g tissue was much greater in the tumor than in other organs. The ratio of uptake of radioactivity (derived from the organ/muscle ratio) was 42.7 (Table 5).

TABLE 1

Immunohistochemical Reactivity of 4G12 Monoclonal Antibody with Various Lung Tumor Tissues

| | | Reactivity | |
|---|---|---|---|
| | Tumor tissues | No. Positive samples | No. Negative samples |
| Primary Lung cancer | Squamous cell carcinoma | 29 | 0 |
| | Adenocarcinoma | 14 | 6 |
| | Adenosquamous cell carcinoma | 1 | 0 |
| | Large cell carcinoma | 3 | 5 |
| | Small cell carcinoma | 0 | 8 |
| Metastatic Lung cancer | Thyroid cancer* | 1 | 0 |
| | Colon cancer* | 1 | 0 |
| | Gastric cancer* | 1 | 0 |
| | Breast cancer* | 0 | 2 |
| | Renal cell carcinoma* | 0 | 2 |
| | Chorioepithelioma* | 0 | 1 |
| Other Lung Tumors | Adenoid cystic carcinoma | 2 | 0 |
| | Carcinoid | 0 | 4 |
| | Hamartoma | 0 | 3 |
| | Sclerosing hamangioma | 0 | 3 |
| Mediastinal Tumors | Thymona | 0 | 5 |
| | Schwannoma | 0 | 5 |
| | Intra thoracic goiter | 0 | 3 |
| | Dermoid cyst | 0 | 2 |

*Primary Tumor

TABLE 2

Immunohistochemical Reactivity of 4G12 Monoclonal Antibody with Normal Tissues

| Normal Tissues | Reactivity | Normal Tissue | Reactivity |
|---|---|---|---|
| Respiratory Tract Organ: | | Endocrinium Organ: | |
| Trachea | +(gland cells) | Pancreas | — |
| Bronchus | +(gland cells) | Thyroid gland | — |
| Peripheral lung tissue | — | Adrenal gland | — |
| Digestive Tract Organ: | | Hematopoietic Organ: | |
| Tongue | — | Erythrocyte | — |
| Esophagus | — | Polymorphonuclear leukocyte | — |
| Stomach | — | Lymphocyte | — |
| Small intestine | — | Bone marrow cells | — |
| Large intestine | — | Spleen | — |
| Liver | — | Lymph node | — |
| Cardio Vasocular System Organ: | | Urinary Tract Organ: | |
| Heart | — | Kidney | ±(tubular cells) |
| Artery | — | Urinary bladder | — |
| Nervous System Organ: | | Reproductive System Organ: | |
| Cerebrum | — | Ovary | — |
| Cerebellum | — | Uterus | — |
| Spinal cord | —(substantia alba or grisea) | Testis | — |
| Peripheral nerve | — | Prostate | — |
| Skin | — | Cross-Striated Muscles | — |
| Mammary Gland | — | | |

TABLE 3

Immunohistochemical Reactivity of 4G12 Monoclonal Antibody with Various nonpulmonary Tumor Tissues

| | | Reactivity | |
|---|---|---|---|
| Tumor Tissues | Histology | No. samples Positive | No. samples Negative |
| Thyroid | Adeno | 1* | 4 |
| Breast | Adeno | 2 | 3 |
| Esophagus | Squamous | 3* | 2 |
| Stomach | Adeno | 2 | 3 |
| Colon | Adeno | 0 | 5 |
| Pancreas | Adeno | 0 | 3 |
| Gall bladder | Adeno | 0 | 3 |
| Extra hepatic bile duct | Adeno | 1 | 4 |
| Liver | Hepato cellular | 0 | 3 |

*Weakly stained

TABLE 4

Immunohistochemical reactivity on various benign tumor tissues

| | Reactivity[a] | |
|---|---|---|
| Tumor Tissues | No. Positive samples | No. Negative samples |
| Lipoma | 0 | 2 |
| Hamartoma | 0 | 4 |
| Dermoid cyst | 0 | 2 |
| Intra-thoracic goiter | 0 | 3 |
| Sclerosing hemangioma | 0 | 3 |

[a]Stained by immunoperoxidase technique.

TABLE 5

Organ distribution of $^{125}$I-labeled 4G12 MoAb in human lung cancer (PC10) bearing nude mice

| Organ | Organ/Muscle ratio |
|---|---|
| Muscle | 1.0[a] |
| Tumor | 42.1 |
| Lung | 1.7 |
| Brain | 0.5 |
| Intestine | 1.8 |
| Liver | 4.8 |
| Bone marrow | 1.9 |
| Heart (Blood) | 6.5 |
| Skin | 5.9 |

[a]Specific radioactivity is 36.9 nCi/g.

(iv) Analysis of antigen recognized by 4G12 monoclonal antibody

On human lung squamous cell carcinoma line (PC10) which showed high reactivity with 4G12 monoclonal antibody, an antigen recognized by the antibody should be present. Based on this, $1 \times 10^8$ of PC 10 cells were labeled with $^{125}$I-Na on the surface of the cellular membrane. Then, its soluble fraction was reacted with the purified monoclonal antibody overnight at 4° C. Thereafter after the reaction product was precipitated using protein A-labeled anti-human IgM antibody. The precipitates were analyzed using SDS-PAGE of 10% polyacrylamide. As a result, 4G12 monoclonal antibody recognized the antigen molecule having a molecular weight of about 200Kd as shown in FIG. 2. Further, this antigen was divided into components having molecular weights of about 65Kd in a reducing condition.

Furthermore, the tumor tissue which showed to be strongly positive to 4G12 monoclonal antibody was treated with 5% periodic acid for 30 minutes, whereby the reactivity was fully lost. From this fact, there is suggested a possibility that sugar chains would take part in its antigenic determinant.

(v) Distribution of recognition antigen

Figure 3:
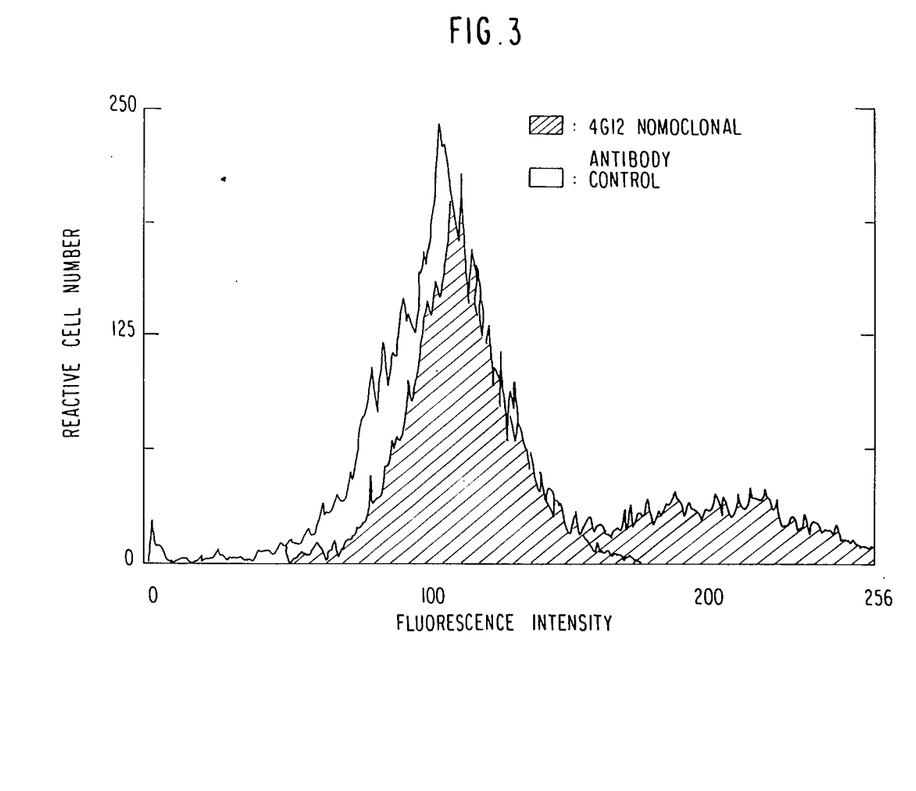
FIG. 3 shows a immunohistochemical staining state of PC10 cells using 4G12 monoclonal antibody.

PC10 cells were subjected to membrane staining using 4G12 monoclonal antibody and the stained state was examined by a cell sorter (FACS). According to this method, PC10 cells, 4G12 monoclonal antibody and FITC-conjugated anti-human IgM antibody were used as a target cell, primary antibody and secondary antibody, respectively and the staining pattern was measured with the cell sorter. As a result, the cells were divided into two groups of non-reactive cell group in which the cells were stained as weakly as the control cells and the reactive cell group in which they were strongly stained, as shown in FIG. 3, and showed a two-phase pattern. The reactive cells were in rates of 25% of PC10 cells. The reactive cells to the 4G12 monoclonal antibody and the non-reactive cells were independently subjected to sorting and the respective cells were separately incubated. The incubated cells were subjected to membrane staining like-wise. As a result, both the reactive cells and the non-reactive cells showed a two-phase pattern as expected.

Moreover, FACS analysis of lung squamous cell line PC10 demonstated that the expression of antigen on the cell surface depended on cell the cycle: maximum in $G_2$ and M phases and minimum in S and $G_1$ phases, suggesting that the antigen recognized by 4G12 monoclonal antibody of the present invention is expressed on the surface of the cells in the proliferative or dividing stages rather than in the resting state.

In addition, the staining pattern of 4G12 monoclonal antibody against lung squamous cell carcinoma suggests that the antigen expression is somehow related to tissue differentiation. 4G12 monoclonal antibody strongly and homogeneously reacts with both membrane and cytoplasm of tumor cells of well-differentiated lung cancer tissues, while heterogenously and rather weakly stained poorly-differentiated tissues. Thus, the antigen recognized by 4G12 monoclonal antibody seems to be a kind of differentiated antigen. These also indicate that 4G12 monoclonal antibody is a good probe for biochemical analysis of profileration and difffferentiation of lung carcinoma cells.

(vi) Cytotoxicity of 4G12 monoclonal antibody

Figure 4:
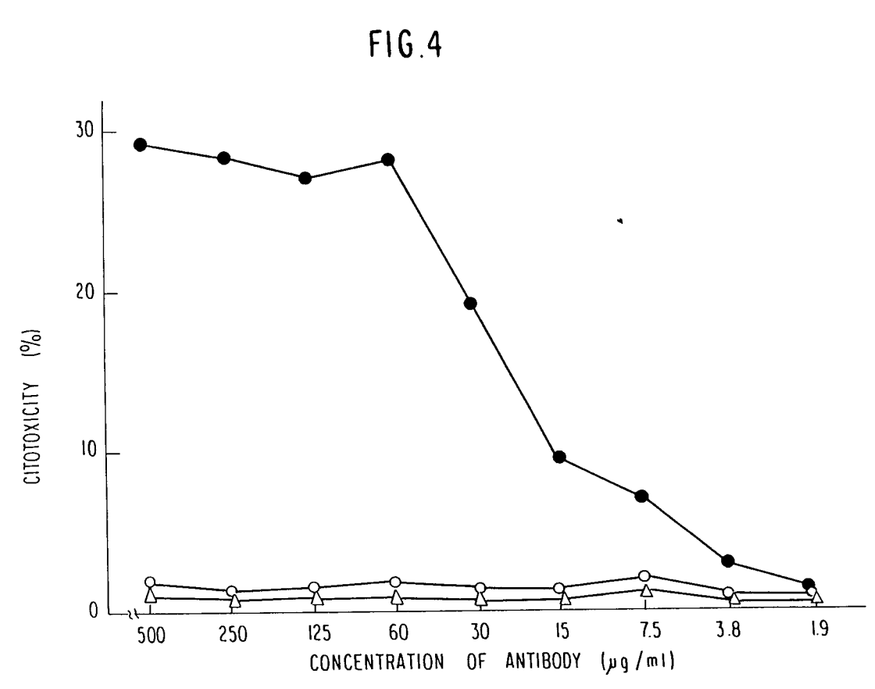

Cytotoxicity of 4G12 monoclonal antibody to PC10 cells as target was assayed by adding complement derived from a guinea pig. Maximum cytotoxicity was in the rates 27% of total cells as shown in FIG. 4. It was suggested that the monoclonal antibody had complment-dependent cytotoxicity.

(9) Stability of 4G12 monoclonal antibody-producing hybridoma

Figure 5:
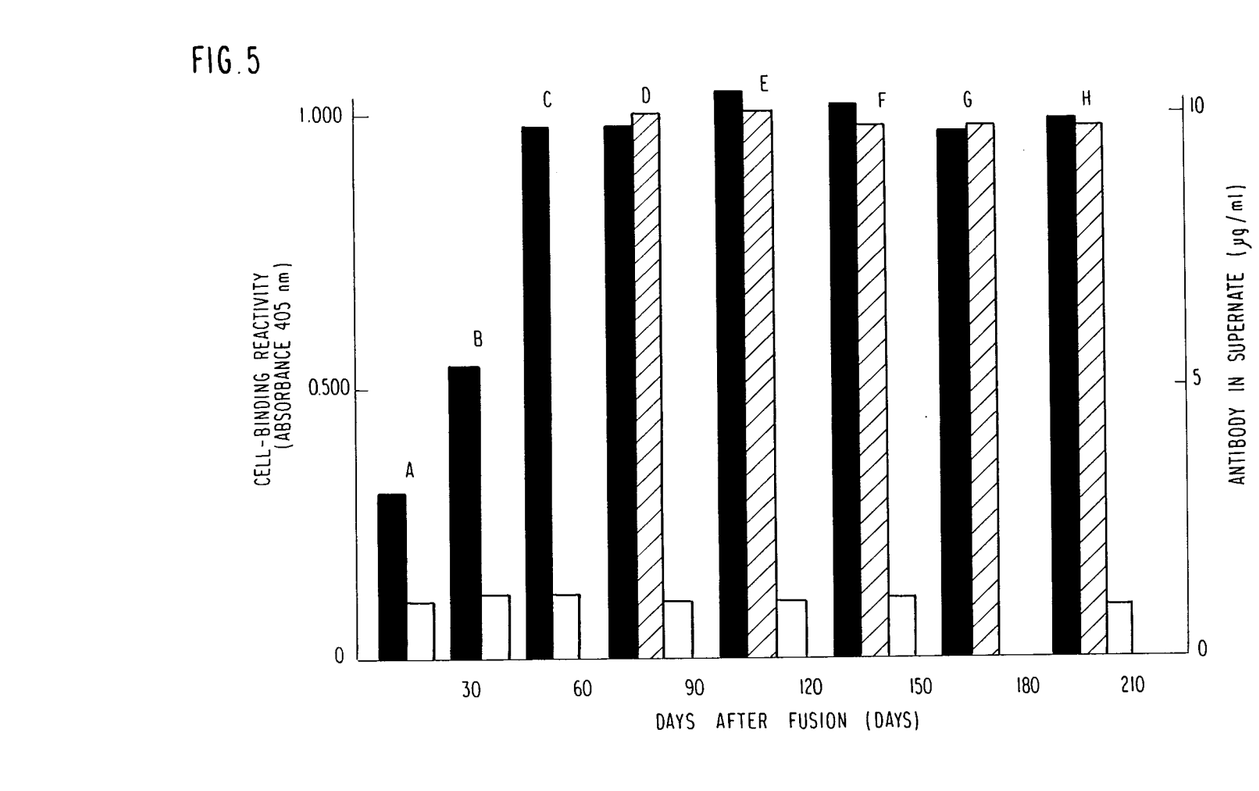

Human-mouse heterohybridoma remarkably causes deletion of human chromosome so that it often discontinues the production of antibody at an early stage even though a fused line producing the desired antibody is obtained. Accordingly, it is believed very difficult to establish a fused line having stability over a long period of time and a high production rate. Therefore, with respect to the hybridoma that secretes 4G12 monoclonal antibody, the antibody concentration produced in the culture supernatant from the time of fusion with passage of day was examined by the ELISA method and further the reactivity of the produced antibody with PC10 cells was measured with ELISA method using cells as target. As a result, a line having a high titer could be obtained only by performing cloning twice at an early stage, as shown in FIG. 5, though any high value was not shown in cell binding assay upon the screening. After establishment of the cell line, the hybridoma secretes the monoclonal antibody very stably without decreasing the antibody productivity even though 24 months passed after the fusion and the antibody concentration (incubation for 2 days) showed 10 μg/ml. Further, the hydridoma also produced a large amount of human monoclonal antibody (4 mg/ml) in nude mice. Therefore, it can be said that the hybridoma has high productivity of the antibody among human-mouse heterohybridomas.

The aforementioned hybridoma producing anti-lung cancer human monoclonal antibody (4G12) was deposited on Mar. 7, 1986 in Institute for Fermentation, Osaka (IFO) under IFO 50090.

What is claimed is:

1. A human monoclonal antibody produced by a human-mouse hybridoma which is obtained by cell fusion of lymph node cells from patients with human squamous lung carcinoma and mouse myeloma cells, said human monoclonal antibody having the following characteristcs:

(1) It reacts with human lung squamous cell carcinoma cell line PC10 and humal lung adenocarcinoma cell line PC 14 but does not react with human adult skin-derived fibroblast cells;

(2) Among tumor slice specimens of tumor tissue removed by operation on a lung cancer patient, it reacts with tissue from lung squamous cell carcinoma, lung adenocarcinoma and lung large cell carcinoma but does not react with tissue from lung small cell cancer and other mediastinal tumors;

(3) It does not react with normal tissues except for trachea gland cells, bronchi gland cells, and kidney renal tubular cells and its does not react with benign tumors;

(4) It reacts with nonpulmonary tumor tissues derived from thyroid cancer, breast cancer, esophagus cancer, stomach cancer and extra hepatic bile duct cancer;

(5) It recognizes an antigen molecule having a molecular weight of about 200Kd as determined by the SDS-PAGE method and found in the soluble fraction on the surface of the cellular membrane of PC10 cells which is divided into components having molecular weights of about 65Kd as determined by the SDS-PAGE method under reducing conditions;

(6) The class of the antibody is IgM and the light chain is lambda.

2. The human monoclonal antibody of claim 1, wherein said antibody is produced by a hybridoma having IFO Accession No. 50090.

3. A human-mouse hybridoma for producing a human monoclonal antibody which is obtained by cell fusion of lymph node cells from patients with human squamous lung carcinoma and mouse myeloma cells, said human monoclonal antibody having the following characteristics:

(1) It reacts with human lung squamous cell carcinoma cell line PC10 and human lung adenocarcinoma cell line PC14 but does not react with human adult skin-derived fibroblast cells;

(2) Among tumor slice specimens of tumor tissue removed by operation on a lung cancer patient, it reacts with tissue from lung squamous cell carcinoma, lung adenocarcinoma and lung large cell carcinoma but does not react with tissue from lung small cell cancer and other mediastinal tumors;

(3) It does not react with normal tissues except for trachae gland cells, bronchi gland cells, and kidney renal tubular cells and it does not react with benign tumors;

(4) It reacts with nonpulmonary tumor tissues derived from thyroid cancer, breast cancer, esophagus cancer, stomach cancer and extra hepatic bile duct cancer;

(5) It recognizes an antigen molecule having a molecular weight of about 200Kd as determined by the SDS-PAGE method and found in the soluble fraction on the surface of the cellular membrane of PC10 cells which is divided into components having molecular weights of about 65Kd as determine by the SDS-PAGE method under reducing conditions;

(6) The class of the antibody is IgM and the light chain is lambda.

4. The hybridoma of claim 3, wherein said hybridoma has IFO Accession No. 50090.

5. An immunoassay for the detection of human lung cancer comprising:

(a) producing the human monoclonal antibody of claim 12;

(b) contacting a sample suspeected of containing human lung cancer tissue with the human monoclonal antibody obtained in step (a) under conditions that allow binding of the human monoclonal antibody to human lung cancer tissue; and (c) assaying for bound human monoclonal antibody.

* * * * *